United States Patent
Podhajsky (10) Patent No.: US 9,539,050 B2
(45) Date of Patent: Jan. 10, 2017

(54) SYSTEM AND METHOD FOR PROCESS MONITORING AND INTELLIGENT SHUT-OFF

(75) Inventor: Ronald J. Podhajsky, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 1009 days.

(21) Appl. No.: 13/085,258

(22) Filed: Apr. 12, 2011

(65) Prior Publication Data

US 2012/0265194 A1    Oct. 18, 2012

(51) Int. Cl.
 *A61B 18/10* (2006.01)
 *A61B 18/12* (2006.01)
 *A61B 18/00* (2006.01)
 *A61B 18/18* (2006.01)

(52) U.S. Cl.
 CPC ........ *A61B 18/1206* (2013.01); *A61B 18/1815* (2013.01); *A61B 2018/00642* (2013.01); *A61B 2018/00648* (2013.01); *A61B 2018/00666* (2013.01); *A61B 2018/00672* (2013.01); *A61B 2018/00678* (2013.01); *A61B 2018/00702* (2013.01); *A61B 2018/00708* (2013.01); *A61B 2018/00779* (2013.01); *A61B 2018/00791* (2013.01); *A61B 2018/00827* (2013.01); *A61B 2018/00869* (2013.01); *A61B 2018/00875* (2013.01); *A61B 2018/00886* (2013.01); *A61B 2018/00892* (2013.01)

(58) Field of Classification Search
 CPC ............ A61B 18/1206; A61B 18/1815; A61B 2018/00642; A61B 2018/00648; A61B 2018/00666; A61B 2018/00672; A61B 2018/00678; A61B 2018/00702; A61B 2018/00708; A61B 2018/00779; A61B 2018/00791; A61B 2018/00827; A61B 2018/00869; A61B 2018/00875; A61B 2018/00886; A61B 2018/00892
 USPC .................................. 606/32, 34, 35, 37–40
 See application file for complete search history.

(56) References Cited

U.S. PATENT DOCUMENTS

| 5,836,943 A | 11/1998 | Miller, III |
| 6,238,387 B1 | 5/2001 | Miller, III |
| 6,464,696 B1 | 10/2002 | Oyama et al. |

(Continued)

FOREIGN PATENT DOCUMENTS

| DE | 179607 | 3/1905 |
| DE | 1099658 | 2/1961 |

(Continued)

OTHER PUBLICATIONS

European Search Report for European Application No. 12002559.8 dated Jul. 12, 2012.

(Continued)

*Primary Examiner* — Michael Peffley
*Assistant Examiner* — Samantha Good (57) ABSTRACT

An electrosurgical generator for supplying electrosurgical energy to tissue is disclosed. The generator includes sensor circuitry configured to measure at least one tissue or energy parameter and a controller configured to generate a plot of the at least one tissue or energy parameter including a plurality of tissue parameter values, wherein the controller is further configured to normalize the plot of the at least one tissue or energy parameter with respect to treatment volume.

9 Claims, 9 Drawing Sheets

(56) References Cited

U.S. PATENT DOCUMENTS

| | | |
|---|---|---|
| 6,648,883 B2 | 11/2003 | Francischelli et al. |
| 6,736,810 B2 | 5/2004 | Hoey et al. |
| 6,796,981 B2 | 9/2004 | Wham et al. |
| 6,849,073 B2 | 2/2005 | Hoey et al. |
| 6,855,141 B2 | 2/2005 | Lovewell |
| 6,962,587 B2 * | 11/2005 | Johnson et al. ............ 606/41 |
| 6,989,010 B2 | 1/2006 | Francischelli et al. |
| 7,137,980 B2 | 11/2006 | Buysse et al. |
| 7,250,048 B2 | 7/2007 | Francischelli et al. |
| 7,303,557 B2 | 12/2007 | Wham et al. |
| 7,364,577 B2 | 4/2008 | Wham et al. |
| 7,367,972 B2 | 5/2008 | Francischelli et al. |
| D574,323 S | 8/2008 | Waaler |
| 7,901,400 B2 | 3/2011 | Wham et al. |
| 2002/0068931 A1 | 6/2002 | Wong et al. |
| 2005/0004564 A1 | 1/2005 | Wham et al. |
| 2005/0203504 A1 * | 9/2005 | Wham et al. .............. 606/34 |
| 2006/0224152 A1 * | 10/2006 | Behnke et al. ............. 606/34 |
| 2007/0038209 A1 | 2/2007 | Buysse et al. |
| 2007/0093800 A1 | 4/2007 | Wham et al. |
| 2007/0173804 A1 | 7/2007 | Wham et al. |
| 2007/0173805 A1 | 7/2007 | Weinberg et al. |
| 2007/0282320 A1 | 12/2007 | Buysse et al. |
| 2008/0015564 A1 | 1/2008 | Wham et al. |
| 2008/0319350 A1 | 12/2008 | Wallace et al. |
| 2009/0157071 A1 | 6/2009 | Wham et al. |
| 2009/0157072 A1 | 6/2009 | Wham et al. |
| 2009/0157075 A1 | 6/2009 | Wham et al. |
| 2009/0259224 A1 | 10/2009 | Wham et al. |
| 2010/0168572 A1 | 7/2010 | Sliwa et al. |
| 2010/0179534 A1 | 7/2010 | Podhajsky et al. |
| 2010/0191233 A1 | 7/2010 | Wham et al. |
| 2010/0211063 A1 | 8/2010 | Wham et al. |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882955 | 12/1998 |
| EP | 1051948 | 11/2000 |
| EP | 1472984 | 11/2004 |
| EP | 1500378 | 1/2005 |
| EP | 1366724 | 1/2006 |
| EP | 880220 | 6/2006 |
| EP | 1776929 | 4/2007 |
| EP | 1810633 | 7/2007 |
| EP | 1810634 | 7/2007 |
| EP | 1862137 | 12/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| JP | 2001037775 A | 2/2001 |
| JP | 2004520865 A | 7/2004 |
| JP | 2009545357 A | 12/2009 |
| JP | 2010279699 A | 12/2010 |
| SU | 166452 | 1/1965 |
| SU | 727201 | 4/1980 |
| WO | WO 98/07378 | 2/1998 |
| WO | WO02/11634 | 2/2002 |
| WO | WO 0232335 | 4/2002 |
| WO | WO02/45589 | 6/2002 |
| WO | WO03/090635 | 11/2003 |
| WO | WO 2004/098385 | 11/2004 |
| WO | WO2006/050888 | 5/2006 |
| WO | WO2008/053532 | 5/2008 |

OTHER PUBLICATIONS

U.S. Appl. No. 10/406,690, filed Apr. 3, 2002, Robert J. Behnke, II.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 12/566,173, filed Sep. 24, 2009, James A. Gilbert.
U.S. Appl. No. 12/566,233, filed Sep. 24, 2009, William N. Gregg.
U.S. Appl. No. 12/567,966, filed Sep. 28, 2009, Craig A. Keller.
U.S. Appl. No. 12/613,876, filed Nov. 6, 2009, Craig A. Keller.
U.S. Appl. No. 12/619,234, filed Nov. 16, 2009, James A. Gilbert.
U.S. Appl. No. 12/639,210, filed Dec. 16, 2009, Jennifer S. Harper.
U.S. Appl. No. 12/712,712, filed Feb. 25, 2010, Mani N. Prakash.
U.S. Appl. No. 12/713,956, filed Feb. 26, 2010, Robert B. Smith.
U.S. Appl. No. 12/715,212, filed Mar. 1, 2010, Robert J. Behnke, II.
U.S. Appl. No. 12/793,136, filed Jun. 3, 2010, Gary M. Couture.
U.S. Appl. No. 12/823,703, filed Jun. 25, 2010, Mark A. Johnston.
U.S. Appl. No. 12/826,879, filed Jun. 30, 2010, Christopher A. Deborski.
U.S. Appl. No. 12/834,364, filed Jul. 12, 2010, David S. Keppel.
U.S. Appl. No. 12/845,203, filed Jul. 28, 2010, Gary M. Couture.
U.S. Appl. No. 12/985,063, filed Jan. 5, 2011, Robert J. Behnke, II.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

(56) References Cited

OTHER PUBLICATIONS

Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10191319.2 dated Feb. 22, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
Japanese Office Action, and English Translation, from Japanese Appl. No. 2012-087418 mailed Dec. 8, 2015.

\* cited by examiner

SYSTEM AND METHOD FOR PROCESS MONITORING AND INTELLIGENT SHUT-OFF

BACKGROUND

Technical Field

The present disclosure relates to electrosurgical apparatuses, systems and methods. More particularly, the present disclosure is directed to electrosurgical systems and methods for monitoring electrosurgical procedures and intelligent termination thereof based on various sensed tissue parameters.

Background of Related Art

Energy-based tissue treatment is well known in the art. Various types of energy (e.g., electrical, ohmic, resistive, ultrasonic, microwave, cryogenic, laser, etc.) are applied to tissue to achieve a desired result. Electrosurgery involves application of radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon that is applied to the tissue. A patient return electrode is placed remotely from the active electrode to carry the current back to the generator.

Ablation is most commonly a monopolar procedure that is particularly useful in the field of cancer treatment, where one or more RF ablation needle electrodes that (usually of elongated cylindrical geometry) are inserted into a living body. A typical form of such needle electrodes incorporates an insulated sheath disposed over an exposed (uninsulated) tip. When the RF energy is provided between the return electrode and the inserted ablation electrode, RF current flows from the needle electrode through the body. Typically, the current density is very high near the tip of the needle electrode, which tends to heat and destroy surrounding issue.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact with body tissue with either of the separated electrodes prevents the flow of current.

Bipolar electrosurgical techniques and instruments can be used to coagulate blood vessels or tissue, e.g., soft tissue structures, such as lung, brain and intestine. A surgeon can either cauterize, coagulate/desiccate and/or simply reduce or slow bleeding, by controlling the intensity, frequency and duration of the electrosurgical energy applied between the electrodes and through the tissue. In order to achieve one of these desired surgical effects without causing unwanted charring of tissue at the surgical site or causing collateral damage to adjacent tissue, e.g., thermal spread, it is necessary to control the output from the electrosurgical generator, e.g., power, waveform, voltage, current, pulse rate, etc.

It is known that measuring the electrical impedance and changes thereof across the tissue at the surgical site provides a good indication of the state of desiccation or drying of the tissue, e.g., as the tissue dries or loses moisture, the impedance across the tissue rises. This observation has been utilized in some electrosurgical generators to regulate the electrosurgical power based on measured tissue impedance.

SUMMARY

An electrosurgical generator for supplying electrosurgical energy to tissue is disclosed. The generator includes sensor circuitry configured to measure at least one tissue or energy parameter and a controller configured to generate a plot of the at least one tissue or energy parameter including a plurality of tissue parameter values, wherein the controller is further configured to normalize the plot of the at least one tissue or energy parameter with respect to treatment volume.

According to an embodiment of the present disclosure, a method for supplying electrosurgical energy to tissue is disclosed. The method includes: measuring at least one tissue or energy parameter; generating a plot of the at least one tissue or energy parameter including a plurality of tissue parameter values; normalizing the plot of the at least one tissue or energy parameter with respect to treatment volume; and regulating output of the electro surgical generator based on the normalized plot of the at least one tissue or energy parameter.

A method for supplying electrosurgical energy to tissue is also contemplated by the present disclosure. The method includes measuring at least one tissue or energy parameter; generating a plot of the at least one tissue or energy parameter including a plurality of tissue parameter values; filtering the plot of the at least one tissue or energy parameter to form a filtered plot of the at least one tissue or energy parameter; normalizing the filtered plot of the at least one tissue or energy parameter with respect to treatment volume; and regulating output of the electrosurgical generator based on the normalized plot of the at least one tissue or energy parameter.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The generator according to the present disclosure can perform monopolar and bipolar electrosurgical procedures as well as microwave ablation procedures and vessel sealing procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

Figure 1A:
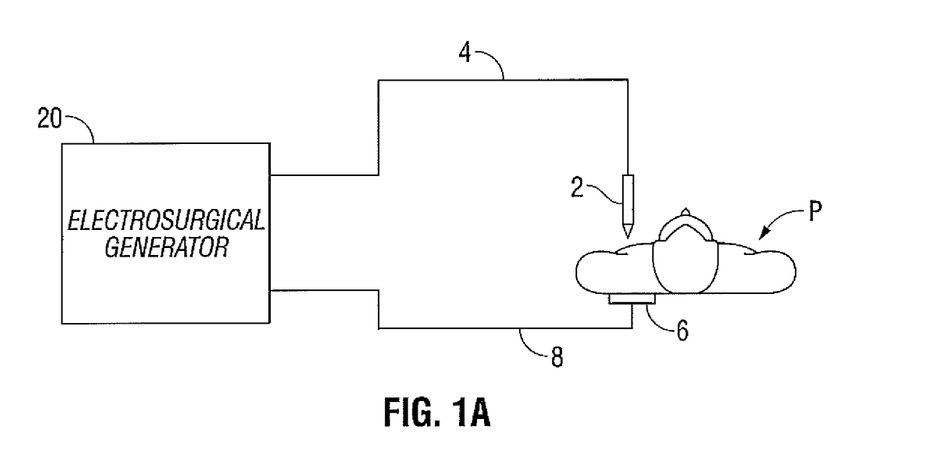
FIG. 1A is a schematic block diagram of a monopolar electrosurgical system according to one embodiment of the present disclosure.

FIG. 1A is a schematic illustration of a monopolar electrosurgical system according to one embodiment of the present disclosure. The system includes an electrosurgical instrument 2 having one or more electrodes for treating tissue of a patient P. The instrument 2 is a monopolar type instrument including one or more active electrodes (e.g., electrosurgical cutting probe, ablation electrode(s), etc.). Electrosurgical RF energy is supplied to the instrument 2 by a generator 20 via an supply line 4, which is connected to an active terminal 30 (FIG. 2) of the generator 20, allowing the instrument 2 to coagulate, ablate and/or otherwise treat tissue. The energy is returned to the generator 20 through a return electrode 6 via a return line 8 at a return terminal 32 (FIG. 2) of the generator 20. The active terminal 30 and the return terminal 32 are connectors configured to interface with plugs (not explicitly shown) of the instrument 2 and the return electrode 6, which are disposed at the ends of the supply line 4 and the return line 8, respectively.

The system may include a plurality of return electrodes 6 that are arranged to minimize the chances of tissue damage by maximizing the overall contact area with the patient P. In addition, the generator 20 and the return electrode 6 may be configured for monitoring so-called "tissue-to-patient" contact to insure that sufficient contact exists therebetween to further minimize chances of tissue damage.

Figure 1B:
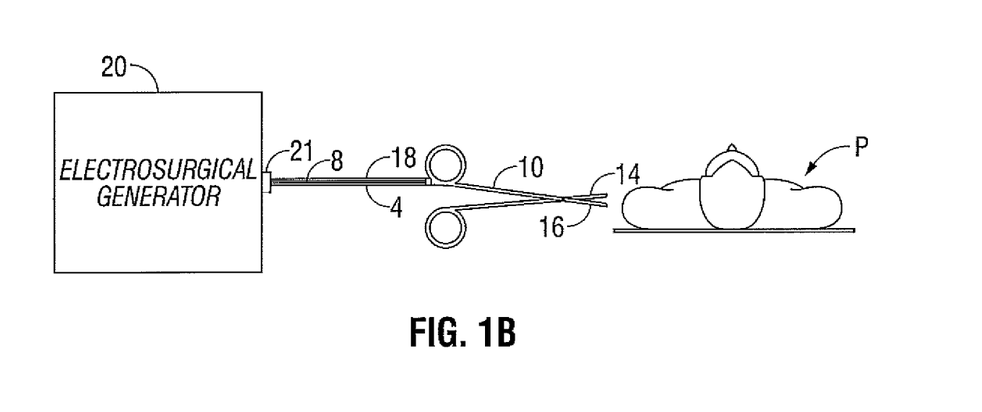
FIG. 1B is a schematic block diagram of a bipolar electrosurgical system according to one embodiment of the present disclosure.
Figure 2:
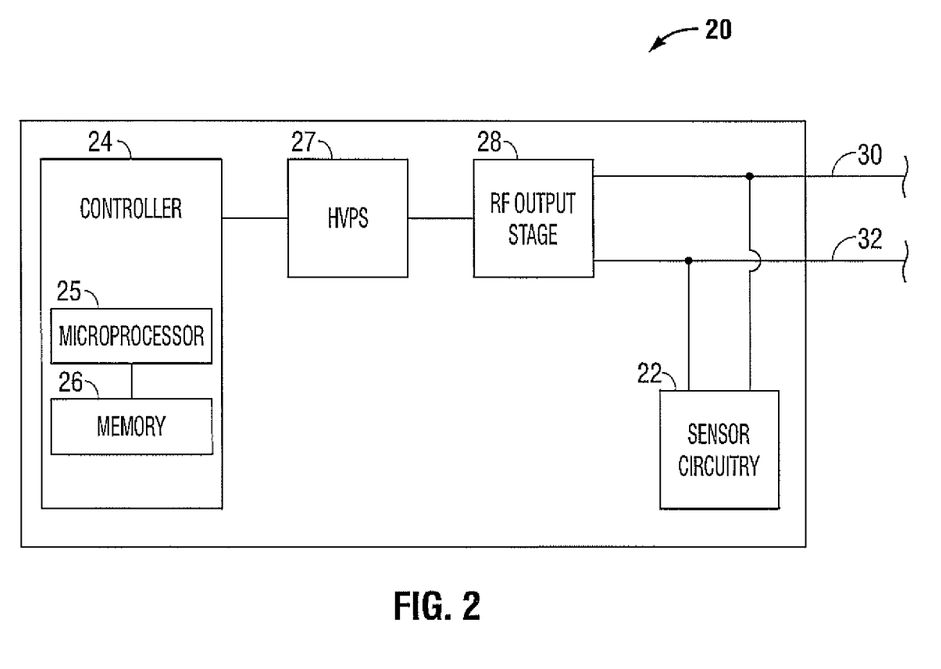
FIG. 2 is a schematic block diagram of a generator according to an embodiment of the present disclosure.

FIG. 1B is a schematic illustration of a bipolar electrosurgical system according to the present disclosure. The system includes a bipolar electrosurgical forceps 10 having one or more electrodes for treating tissue of a patient P. The electrosurgical forceps 10 includes opposing jaw members having an active electrode 14 and a return electrode 16 disposed therein. The active electrode 14 and the return electrode 16 are connected to the generator 20 through cable 18, which includes the supply and return lines 4, 8 coupled to the active and return terminals 30, 32, respectively (FIG. 2). The electrosurgical forceps 10 is coupled to the generator 20 at a connector 21 having connections to the active and return terminals 30 and 32 (e.g., pins) via a plug disposed at the end of the cable 18, wherein the plug includes contacts from the supply and return lines 4, 8.

The generator 20 includes suitable input controls (e.g., buttons, activators, switches, touch screen, etc.) for controlling the generator 20. In addition, the generator 20 may include one or more display screens for providing the user with variety of output information (e.g., intensity settings, treatment complete indicators, etc.). The controls allow the user to adjust power of the RF energy, waveform parameters (e.g., crest factor, duty cycle, etc.), and other parameters to achieve the desired waveform suitable for a particular task (e.g., coagulating, tissue sealing, intensity setting, etc.). The instrument 2 may also include a plurality of input controls that may be redundant with certain input controls of the generator 20. Placing the input controls at the instrument 2 allows for easier and faster modification of RF energy parameters during the surgical procedure without requiring interaction with the generator 20.

FIG. 2 shows a schematic block diagram of the generator 20 having a controller 24, a high voltage DC power supply 27 ("HVPS") and an RF output stage 28. The HVPS 27 is connected to a conventional AC source (e.g., electrical wall outlet) and provides high voltage DC power to an RF output stage 28, which then converts high voltage DC power into RF energy and delivers the RF energy to the active terminal 30. The energy is returned thereto via the return terminal 32.

In particular, the RF output stage 28 generates sinusoidal waveforms of high RF energy. The RF output stage 28 is configured to generate a plurality of waveforms having various duty cycles, peak voltages, crest factors, and other suitable parameters. Certain types of waveforms are suitable for specific electrosurgical modes. For instance, the RF output stage 28 generates a 100% duty cycle sinusoidal waveform in cut mode, which is best suited for ablating, fusing and dissecting tissue and a 1-25% duty cycle waveform in coagulation mode, which is best used for cauterizing tissue to stop bleeding.

The generator 20 may include a plurality of connectors to accommodate various types of electrosurgical instruments (e.g., instrument 2, electrosurgical forceps 10, etc.). Further, the generator 20 is configured to operate in a variety of modes such as ablation, monopolar and bipolar cutting coagulation, etc. It is envisioned that the generator 20 may include a switching mechanism (e.g., relays) to switch the supply of RF energy between the connectors, such that, for instance, when the instrument 2 is connected to the generator 20, only the monopolar plug receives RF energy.

The controller 24 includes a microprocessor 25 operably connected to a memory 26, which may be volatile type memory (e.g., RAM) and/or non-volatile type memory (e.g., flash media, disk media, etc.). The microprocessor 25 includes an output port that is operably connected to the HVPS 27 and/or RF output stage 28 allowing the microprocessor 25 to control the output of the generator 20 according to either open and/or closed control loop schemes. Those skilled in the art will appreciate that the microprocessor 25 may be substituted by any logic processor (e.g., control circuit) adapted to perform the calculations discussed herein.

A closed loop control scheme is a feedback control loop wherein sensor circuitry 22, which may include a plurality of sensors measuring a variety of tissue and energy properties (e.g., tissue impedance, tissue temperature, output current and/or voltage, voltage and current passing through the tissue, etc.), provides feedback to the controller 24. Such sensors are within the purview of those skilled in the art. The controller 24 then signals the HVPS 27 and/or RF output stage 28, which then adjust DC and/or RF power supply, respectively. The controller 24 also receives input signals from the input controls of the generator 20 or the instrument 2. The controller 24 utilizes the input signals to adjust power outputted by the generator 20 and/or performs other control functions thereon.

The present disclosure provides for a system and method for monitoring electrosurgical procedures using one or more tissue parameters, which include real impedance, imaginary impedance, phase angle, voltage, current, average power and combinations thereof. The use of tissue parameters to control delivery of electrosurgical energy is discussed with respect to performing ablation procedures, however, those skilled in the art will appreciate that the illustrated embodiments may be utilized with other electrosurgical procedures and/or modes.

Figure 3:
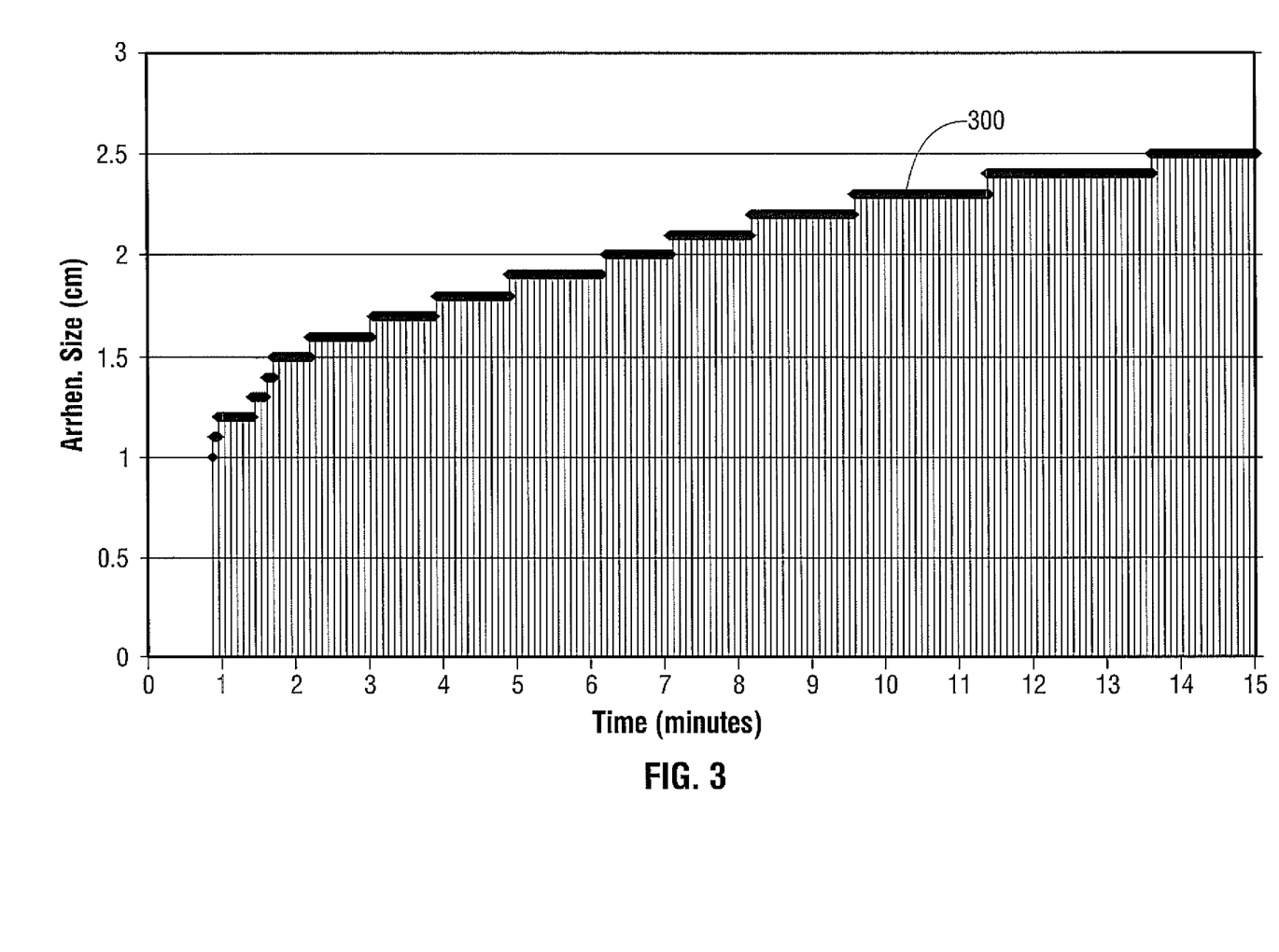
FIG. 3 is a plot of treatment volume during application of electrosurgical energy according to one embodiment of the present disclosure.

In embodiments, various tissue parameters may be measured, recorded and then plotted to form tissue parameter plots. The tissue parameter plots are then filtered to obtain a filtered curve that correlates to the size of the ablation volume. In particular, FIG. 3 shows a plot 300 of an treatment volume calculated based on temperature measurements. The treatment volume may be estimated using an Arrhenius ablation model implemented via LABVIEW™ software, which is available from National Instruments of Austin, Tex. The software may be executed on a variety of computing devices, such as Luxtron thermal probes available from LumaSense Technologies of Santa Clara, Calif., that may also interface with a plurality of suitable temperature measurement devices that provide temperature measurements over a predetermined period of time (e.g., about 15 minutes) to the computing device. The probes may be disposed at multiple locations to provide for different temperature measurements which allows for extrapolation of the size of the ablation volume. The software then calculates the estimated treatment volume based on the models discussed above that are implemented in the software. In embodiments, the size of the ablation volume may also be determined by excising the volume, obtaining a plurality of slices of the ablation volume and measuring the cross-sectional size of the ablation volume of each of the slices. This procedure may be performed to verify the accuracy of the modeled treatment volume as determined by the Arrhenius ablation model.

Figure 4:
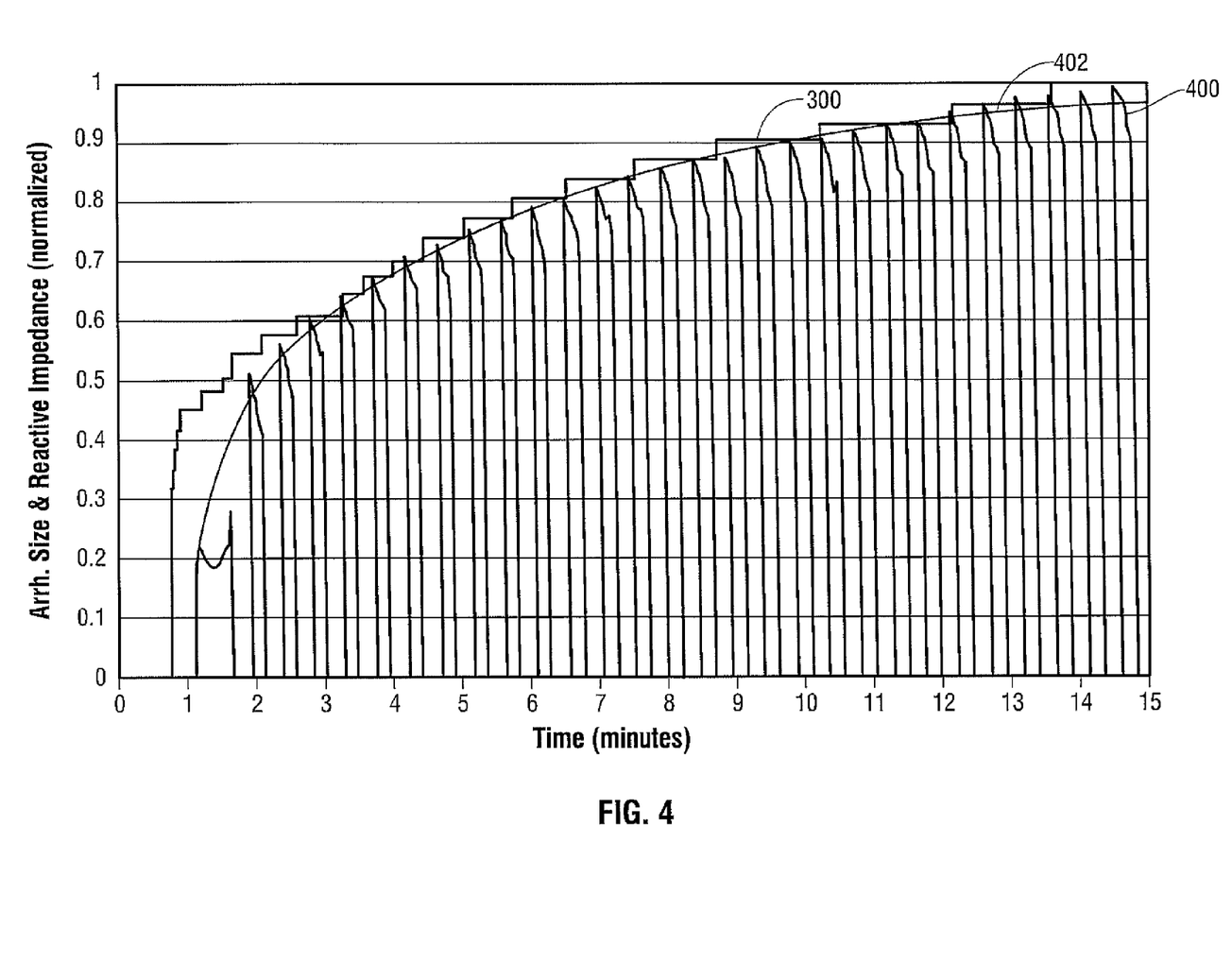
FIG. 4 is a plot of treatment volume and impedance during application of electrosurgical energy according to one embodiment of the present disclosure.

FIGS. 4-8 illustrate plots of various tissue parameters. FIG. 4 shows a plot 400 of reactive impedance. Plot 400 is obtained by normalizing a plot of imaginary (e.g., reactive) impedance vs. time. The imaginary impedance values are filtered prior to normalization, which may be accomplished by assigning 1 to an ending value of the plot 400 and 0 to the starting value. The plot 400 may be smoothed by convolution and the peaks may then be detected by using an extrema function. Connecting the peaks of the plot 400 provides for a correlated plot 402, which substantially matches the shape of the treatment volume plot 300. This may be accomplished by curve-fitting using a spline function and then correlating the two plots 300 and 402. These functions may be performed by using MATLAB™ environment, which provides for convolution, extrema, curve fitting, and correlation functions, available from Mathworks of Natick, Mass. In particular, the correlation value, $\rho$, for the plot 402 with the plot 300 was about 1, which denotes a high degree of correlation.

Figure 5:
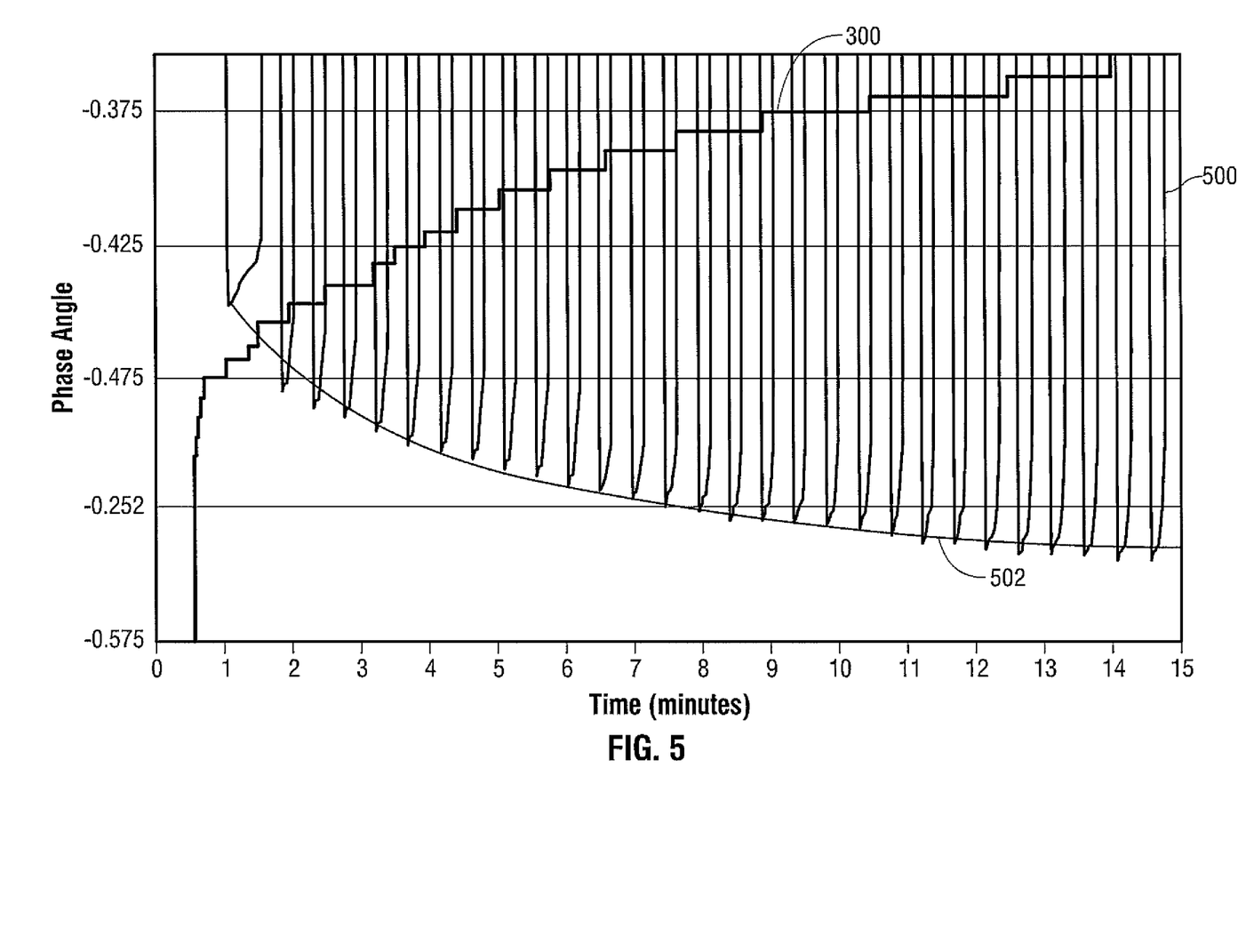
FIG. 5 is a plot of phase angle during application of electrosurgical energy according to one embodiment of the present disclosure.
Figure 6:
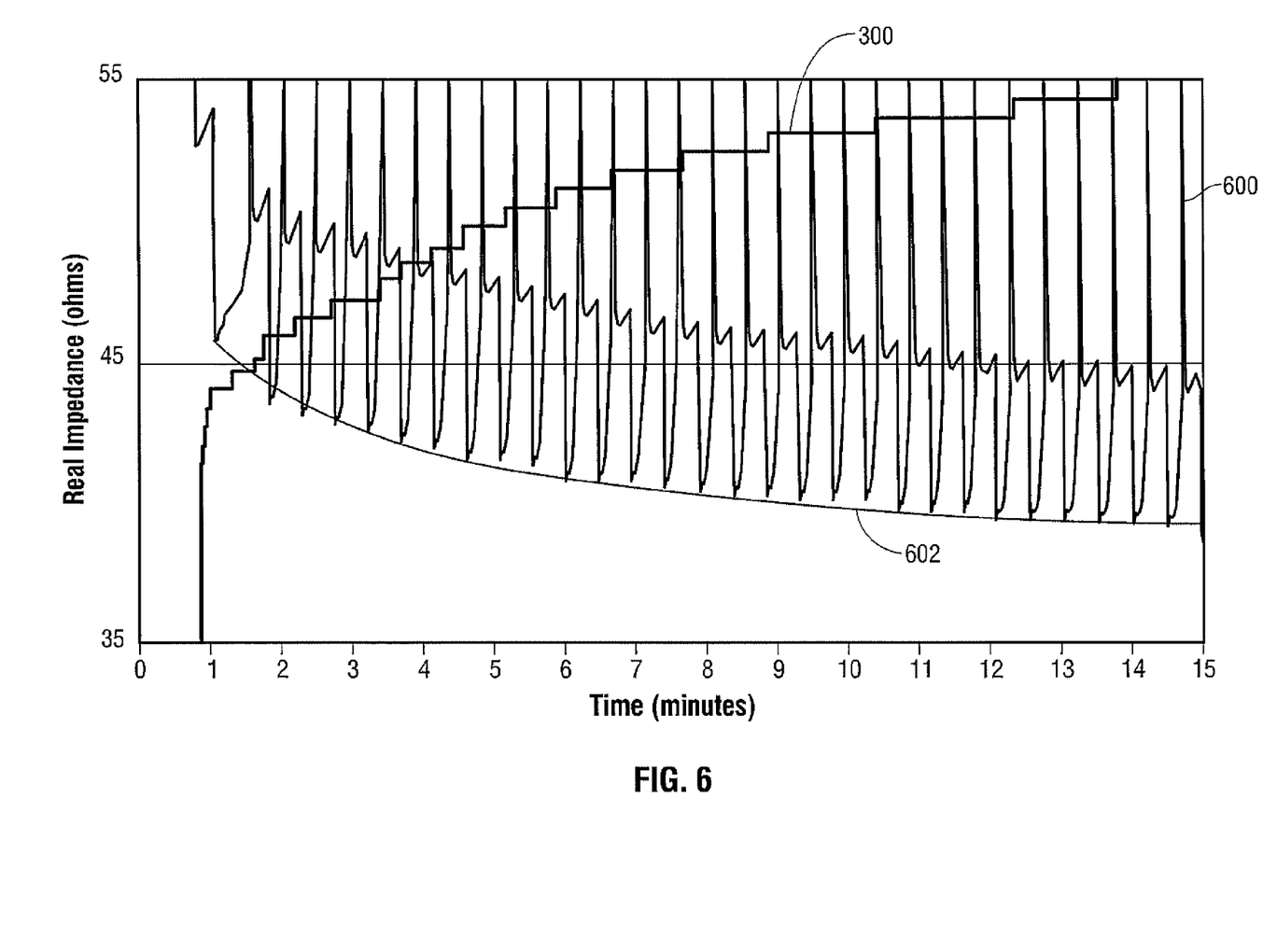
FIG. 6 is a plot of real impedance during application of electrosurgical energy according to one embodiment of the present disclosure.
Figure 7:
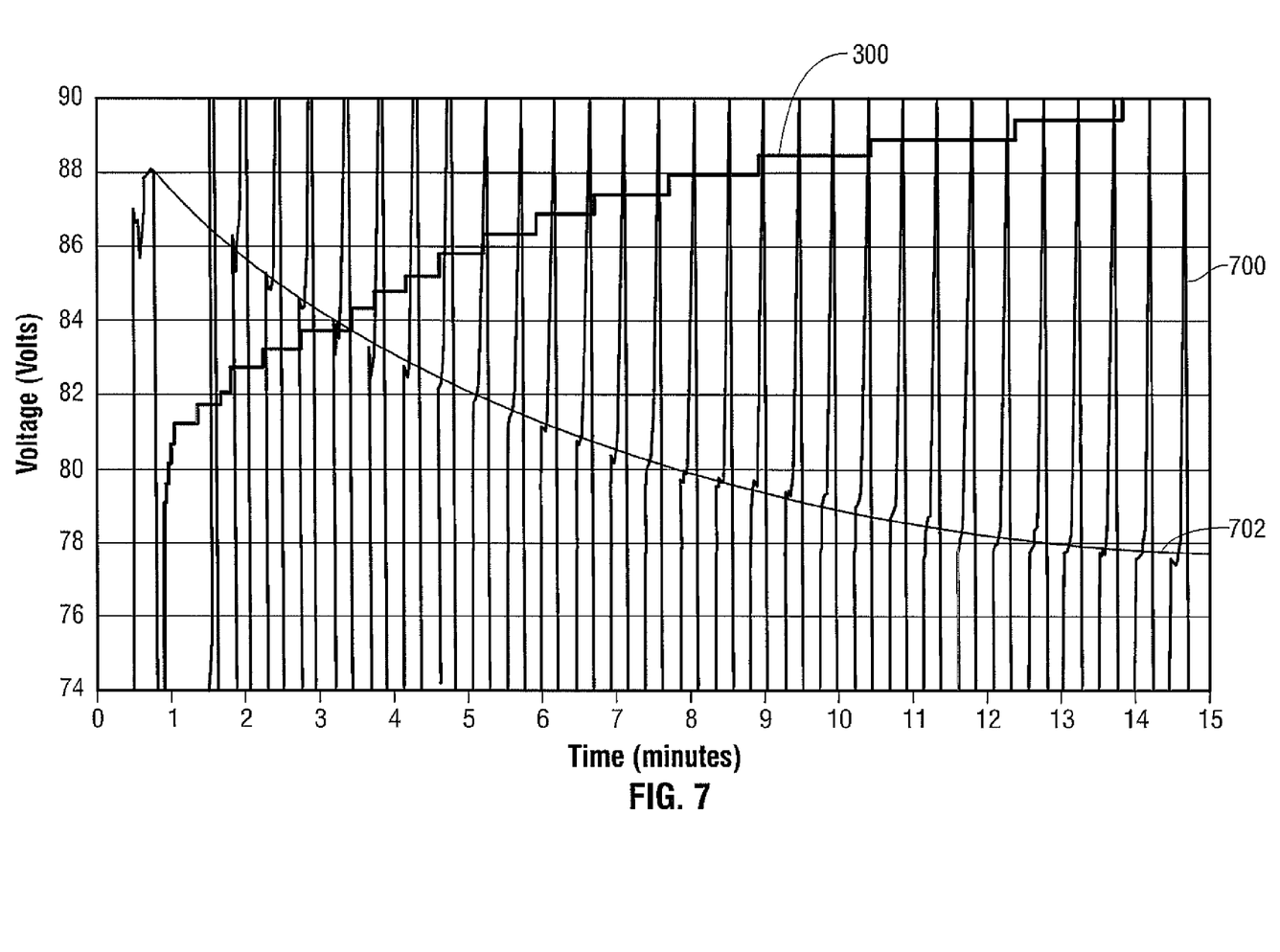
FIG. 7 is a plot of voltage during application of electrosurgical energy according to one embodiment of the present disclosure.
Figure 8:
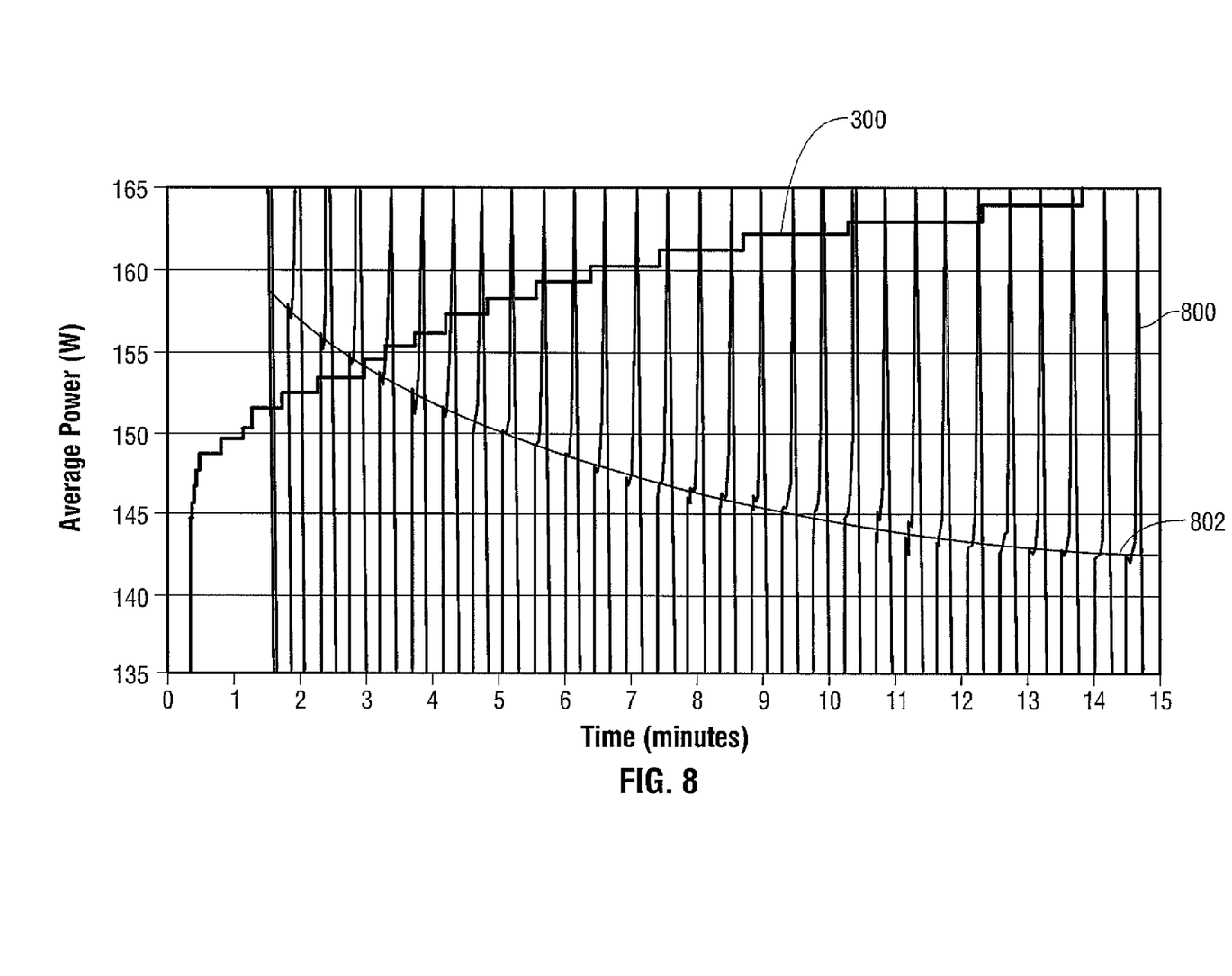
FIG. 8 is a plot of average power during application of electrosurgical energy according to one embodiment of the present disclosure.

Similar correlation is also illustrated by FIGS. 5-8. In particular, FIG. 5 shows a plot 500 of phase angle measurements, which is also normalized. Connecting the peaks of the plot 500 provides for a correlated plot 502, which when inverted substantially matches the shape of the plot 300. FIGS. 6-8 show a plot 600 of real impedance, a plot 700 of voltage, and a plot 800 of average power, respectively, all of which are scaled. Connecting the peaks of the plot 600 provides for a correlated plot 602, which when inverted also substantially matching the plot 300. The plots 702 and 802 may be generated based on ripples found at about the midpoint of the leading rising or falling edge of each of the peaks of the plots 700 and 800, respectively. Ripples may be identified as any fluctuations in the peak aside from the peak itself. The resulting plots are also inverted to provide for the correlated plots 702 and 802.

The relationship between the plots 402, 502, 602, 702, 802 and 300 illustrates the correlation between various tissue parameters, such as reactive impedance, phase angle, real impedance, voltage and average power and the size of the ablation as determined using temperature measurements.

Similar to the correlation value of the plot 402 with the plot 300, the correlation value for the plots 502 and 602 with the plot 300 was also about 1. This illustrates, that imaginary impedance, real impedance and phase angle yield patterns that are highly correlated with treatment volume dynamics and are suitable for detecting process progression and possible trigger points for initiating procedure termination. Although each of the tissue parameters appears to be correlated to the treatment volume (i.e., ablation volume), while not wishing to be bound by theory, it is believed that each of the tissue parameters may be measuring different characteristics of tissue consistency.

Complex impedance consists of real and imaginary impedance. Real impedance is identified with resistance and imaginary impedance is identified with reactance. In addition, reactive impedance may be either inductive or capacitive. Purely resistive impedance exhibits no phase shift between the voltage and current, whereas reactance induces a phase shift $\theta$ between the voltage and the current passing through the tissue, thus imaginary impedance may be calculated based on the phase angle or phase shift between the voltage and current waveforms.

Changes in the imaginary impedance during energy delivery may be used as an indication of changes in tissue properties due to energy application. More specifically, imaginary impedance may be used to detect the formation of micro bubbles, bubble fields and tissue desiccation that impart an electrical reactivity to the tissue that corresponds to sensed imaginary impedance. The tissue reactivity is reflective of the energy that is being delivered into the tissue. Thus, the measured change in imaginary impedance may be used as an indication of the amount of energy resident in the tissue. Monitoring of the resident energy in combination with monitoring of the energy being supplied by the generator allows for calculation of energy escaping the tissue during treatment, thereby allowing for determination of efficiency of the treatment process as well as any inadvertent energy drains.

As the ablation volume increases, so does the region of tissue that can support formation of micro bubbles. The presence of micro bubbles in soft tissue increases the capacitance of the dielectric character of the affected tissue. As the energy being applied to the tissue increases, the micro bubbles then accrete to form macro bubbles, which decreases the capacitance but increases real impedance of the tissue. Hence, the shift of bubble population from micro to macro levels is indicated by a shift of measured impedance from reactive to real. One consequence of this is that water content of the tissue is displaced by this transformation and that displaced water may be harnessed to create desired tissue effects (e.g., tissue division).

Figure 9:
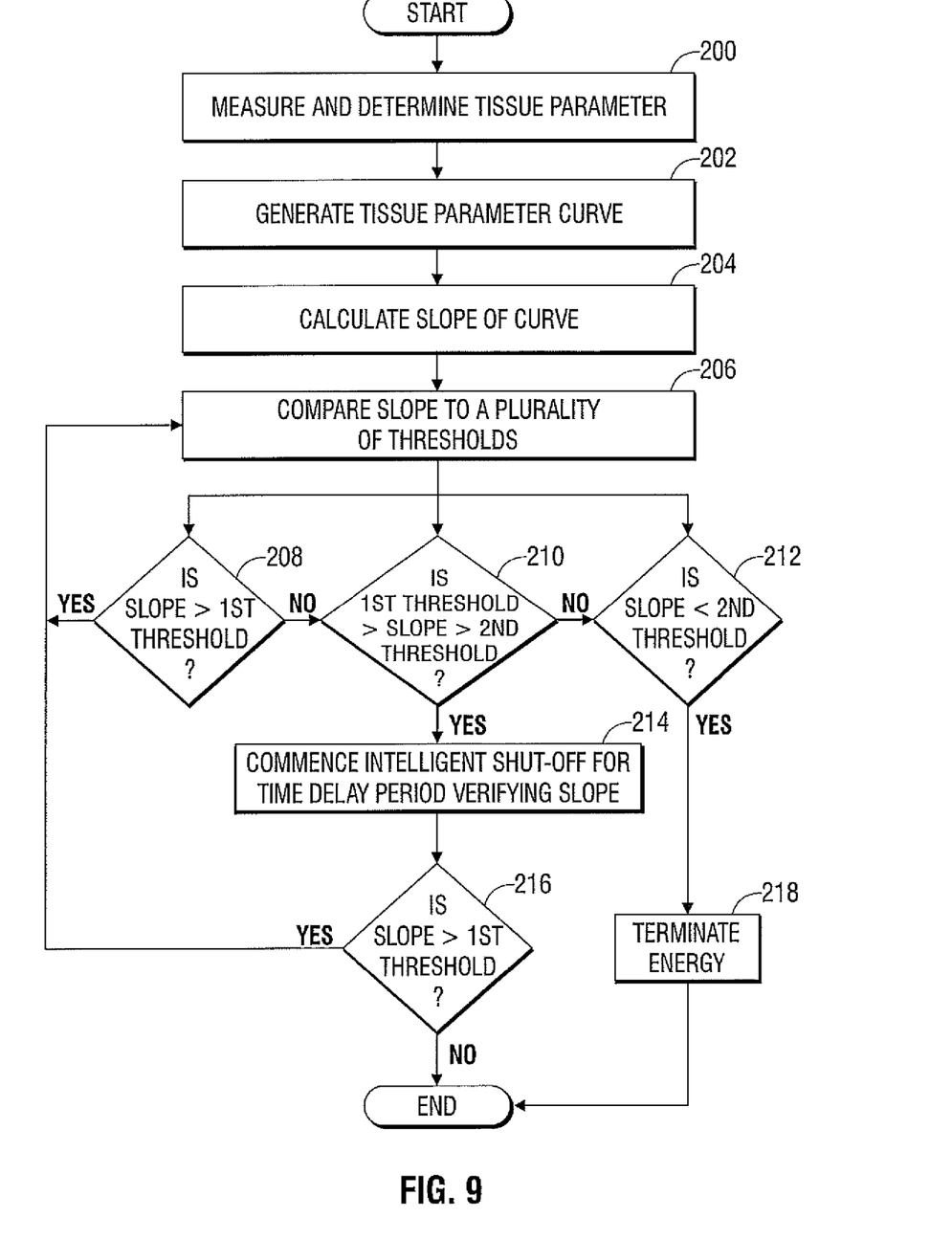
FIG. 9 is a flow chart of a method according to one embodiment of the present disclosure.

FIG. 9 shows a method for controlling output of the generator 20 based on various tissue parameters. The method may be embodied as a software application embedded in the memory 26 and executed by the microprocessor 25 to control generator 20 output based on measured tissue parameters or changes thereof as a function of time. In step 200, ablation energy is delivered into tissue and various tissue parameters are measured by the sensor circuitry 22. In particular, the sensor circuitry 22 measures tissue and energy parameters based on voltage and current waveforms passing through the tissue and determines voltage, current, average power, phase angle between the waveforms, real impedance, and imaginary impedance (e.g., the imaginary component of the complex impedance) based on the phase angle between the waveforms.

In step 202, the tissue and energy parameters are measured and are plotted in real-time to generate a tissue or energy parameter plot as shown in FIGS. 4-8. The plot is pre-filtered to allow for faster processing to generate a pre-filtered curve having smoother curves. Various filters may be utilized to achieve the pre-filtered curve, such as Kalman Filter and the like. The plot is also normalized as discussed above, thereafter, the peaks are detected and are interconnected to produce a correlated plot as shown in FIG. 4. The peaks are detected by the generator 20 by recording an amplitude value of a specific tissue or energy parameter (e.g., reactive impedance) corresponding to the peak. The peaks may be identified by tracking the changes in the rate of change, e.g., slope of the plotted tissue or energy parameter plot, e.g., plot 400.

In embodiments, as shown in FIGS. 5 and 6, the plot may also be inverted to correlate with the treatment volume plot. In further embodiments, as shown in FIGS. 7 and 8, the plot may be generated based on the ripples of each of the peaks. The ripples on the rising edge in both voltage and average power plots 700 and 800, respectively are due to the energy being pulsed. The ripples may be detected based on radical changes in the slope (e.g., rapid oscillations between positive and negative values during a rising edge). The rising or falling edge may also be identified by tracking a positive or negative slope, respectively, for a predetermined period of time. The generator 20 then records the amplitude values of the tissue or energy parameter corresponding to ripples and generates a plot therethrough. In embodiments, the plot may also be inverted.

As the curve is generated, it may be analyzed to determine a shut-off point. As discussed above, as energy is applied to the tissue, micro bubbles form in the intracellular and intercellular space, resulting in a low starting imaginary impedance (e.g., more negative, associated with more inductive). As the temperature of the tissue increases, liquid water is driven away from the tissue regions close to a phase transition temperature (e.g., 80° C. and above), more micro bubbles form, steam bubbles increase in size and these regions become desiccated. The desiccated regions of tissue have higher impedance and therefore contribute to the capacitive impedance. These phenomena are mostly reversible because as the temperature increases and drives the water out, osmotic pressures generate a reverse flow of water. As a result, the tissue seeks a new equilibrium or steady state condition between a desiccated state and a hydrated state to reestablish energy balance.

Once the equilibrium is achieved, the thermal kill zone (e.g., treatment volume) does not grow significantly. Thus, establishment of equilibrium correlates to the maximum thermal kill zone and may be used to determine whether termination of energy application is appropriate. In other words, monitoring of imaginary impedance allows for determination of the equilibrium, which correlates with the maximum thermal kill zone and may therefore, serve as a suitable threshold of intelligent shut-off.

Determination of the equilibrium may be determined by analyzing the slope of the tissue parameter curve or the rate of change of the imaginary impedance. The determination of the slope may be performed at the sensor circuitry 22 and/or the controller 24. A slope of about 0 is believed to be reflective of the establishment of equilibrium, whereas a negative slope corresponds to reduction in energy accumulation within the tissue. Prior to slope analysis, the tissue parameter curve is filtered using a single pole recursive filter. Thus, the first filter smoothes out the impedance curve 110 and the recursive filtering detects direction and magnitude of the slope changes as described below.

In step 204, the slope of the tissue parameter curve (e.g., rate of change of the tissue parameter) is determined. According to one embodiment of the present disclosure, the determination of the rate of change may be achieved via single pole recursive filtering that averages a predetermined number of tissue parameter values to achieve the rate of change value. Any number of impedance filters may be used and are based on the following formula (I):

$$ZfX_n = Zin*A + ZfX_{n-1}*B \qquad (1)$$

A and B are dependent on a time constant and may be specified by the user, via the input controls of the generator 20, for each particular impedance filter ZfX. When calculating A and B, the following formulas may be used:

$$B = e^{\wedge}(-1/\text{number of samples});$$

$$A = 1 - B.$$

The sample rate may also be specified by the user for calculating the number of samples. In formula (I), Zin is the new root mean square tissue parameter value (e.g., $Zi_{RMS}$) just calculated, and $ZfX_{n-1}$ is the filtered tissue parameter, for the filter number specified by X, from the previous iteration through the loop, and $ZfX_n$ is the new filtered impedance value for the filter number specified by X. In one embodiment, the sample rate for calculating the number of samples may be synchronized with the loop time of the microprocessor 25. Accordingly, within about 5 time constants, the final output of the tissue parameter filter may be provided that corresponds to the slope of the tissue parameter curve. In another embodiment, an initial base tissue parameter may be used to preload the tissue parameter filters.

In step 206, the slope of the tissue parameter curve is analyzed. In one embodiment, the slope is analyzed using three regions (e.g., two thresholds). In step 208, it is determined whether the slope is above a first predetermined threshold (e.g., a positive threshold number). In step 210 it is determined whether the slope is between the first threshold and a second predetermined threshold (e.g., a negative number). In step 212, it is determined if the slope is below the second threshold. In another embodiments, a plurality of regions may be utilized based on multiple actions that need to be performed in response to varying slope values. Based on the analysis of the rate of change of the tissue parameter (e.g., slope) and/or the tissue parameter, the controller 24 adjusts the output of the generator 20 as discussed in more detail below.

When the slope is above the first threshold, this indicates that the thermal profile is growing and that energy application may continue in step 208. The process then reverts to step 206 to continue slope monitoring and energy application. When the slope is between the first and second thresholds, the thermal profile is in equilibrium which denotes that equilibrium has been reached and an intelligent shut-off process is commenced as shown in step 214. Once it is determined that equilibrium has been reached, a verification is made if a predetermined time delay has expired. This provides a second verification to determine that a substantial portion of the tissue has been treated. The time delay may be user-selectable either by entering a predetermined time value or by selecting one of proposed delay periods. In one embodiment, one of the options may be a time delay corresponding to the shortest time for establishing termination of the procedure and another option may be a time delay corresponding to a conservative treatment regimen that assurance 100% cell kill ratio.

In one embodiment, an intermediate time delay may also be utilized. An intermediate time delay is triggered in step 216 once an equilibrium is reached and the slope detection still continues to make sure that the slope trends do not change. If the slope increases above the first threshold, then energy application resumes. At this point, the intermediate time delay is triggered and slope interrogation continues. In other words, the process then reverts to step 206 to continue slope monitoring and energy application.

When the slope is less than the second threshold, this denotes that energy application efficiency is decreasing and the procedure should be terminated. This may be caused by proximity to a blood vessel and other obstructions. Upon encountering negative slopes that are below the second threshold, the process in step 218 terminates the application of energy and/or alerts the user of the decrease in energy application.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator for supplying electrosurgical energy to tissue, comprising:
    sensor circuitry configured to measure at least one tissue or energy parameter; and
    a controller configured to:
        generate a first plot of the at least one tissue or energy parameter including a plurality of peaks;
        detect the plurality of peaks;
        interconnect the plurality of peaks to generate an interconnected plot; and
        normalize the interconnected plot with respect to treatment volume.

2. The electrosurgical generator according to claim 1, wherein the at least one tissue or energy parameter is selected from the group consisting of imaginary impedance, real impedance, phase angle, voltage, current and average power.

3. The electrosurgical generator according to claim 1, wherein the controller is further configured to regulate output of the electrosurgical generator based on the normalized interconnected plot of the at least one tissue or energy parameter.

4. The electrosurgical generator according to claim 1, wherein the controller is further configured to filter the first plot of the at least one tissue or energy parameter.

5. The electrosurgical generator according to claim 4, wherein the controller is further configured to execute at least two recursive filters configured to recursively process the first plot of the at least one tissue or energy parameter.

6. The electrosurgical generator according to claim 1, wherein the controller is configured to regulate the electrosurgical generator based on a rate of change of the at least one tissue or energy parameter and is configured to control the electrosurgical generator to continue application of the electrosurgical energy when the rate of change of the at least one tissue or energy parameter is above a first predetermined threshold.

7. The electrosurgical generator according to claim 6, wherein the controller is configured to regulate the electrosurgical generator to discontinue application of the electrosurgical energy when the rate of change of the at least one tissue or energy parameter is below a second predetermined threshold.

8. The electrosurgical generator according to claim 7, wherein the controller is configured to regulate the electrosurgical generator to commence intelligent shut-off of the electrosurgical energy for a duration of a predetermined time delay when the rate of change of the at least one tissue or energy parameter is between the first and second predetermined thresholds.

9. The electrosurgical generator according to claim 8, wherein the controller is configured to regulate the electrosurgical generator to restart application of the electrosurgical energy when the rate of change of the at least one tissue or energy parameter is above the first predetermined threshold during the time delay.

* * * * *